(12) United States Patent
Desai et al.

(10) Patent No.: US 8,968,614 B2
(45) Date of Patent: Mar. 3, 2015

(54) METHOD OF MAKING HIGH-ELONGATION APERTURED NONWOVEN WEB

(75) Inventors: Fred N. Desai, Fairfield, OH (US); Hiroshi Nakahata, Kobe (JP); John J. Curro, Cincinnati, OH (US); Douglas H. Benson, West Harrison, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 2003 days.

(21) Appl. No.: 11/321,347

(22) Filed: Dec. 29, 2005

(65) Prior Publication Data

US 2006/0107505 A1 May 25, 2006

Related U.S. Application Data

(62) Division of application No. 09/909,486, filed on Jul. 20, 2001, now abandoned.

(51) Int. Cl.
*B29C 55/14* (2006.01)
*A61F 13/512* (2006.01)
(Continued)

(52) U.S. Cl.
CPC ............ *A61F 13/512* (2013.01); *B29C 55/146* (2013.01); *A61F 2013/51322* (2013.01); *D04H 1/5405* (2013.01); *D06C 3/00* (2013.01)
USPC ..................... 264/154; 264/210.7; 264/288.8; 264/290.2

(58) Field of Classification Search
USPC .......................... 264/154, 210.7, 288.8, 290.2
See application file for complete search history.

(56) References Cited

U.S. PATENT DOCUMENTS

| 3,860,003 A | 1/1975 | Buell |
| 4,223,059 A | 9/1980 | Schwarz |

(Continued)

FOREIGN PATENT DOCUMENTS

| EP | 0 127 483 A2 | 12/1984 |
| EP | 955 159 A1 | 11/1999 |

(Continued)

*Primary Examiner* — Leo B Tentoni
(74) *Attorney, Agent, or Firm* — William E. Gallagher; Andrew A Paul; Charles R. Ware

(57) ABSTRACT

An extensible apertured nonwoven web, and a method for making such an apertured nonwoven web. In one embodiment the method comprises the steps of providing an apertured nonwoven web, incrementally stretching it in a direction substantially parallel to the cross machine direction, and applying tension in the machine direction such that the web width after applying tension is less than the web width after incremental stretching. In another embodiment the method comprises the steps of providing a nonwoven web; weakening the nonwoven web at a plurality of locations to create a plurality of weakened, melt-stabilized locations; applying a first tensioning force to the nonwoven web to cause the nonwoven web to rupture at the plurality of weakened, melt-stabilized locations creating a plurality of apertures in the nonwoven web coincident with the weakened, melt-stabilized locations, incrementally stretching the nonwoven web in a direction substantially parallel to the cross machine direction, and applying tension in the machine direction such that the web width after applying machine direction tension is less than the web width after incremental stretching. An apparatus for producing a web of the present invention by this method is also disclosed. The extensible apertured nonwoven web produced has a plurality of apertures each having a hole size greater than 2 mm$^2$, and a hole aspect ratio less than 6, the nonwoven web having an open area greater than 15% and being capable of at least 70% extension in the cross machine direction at a loading of 10 g/cm.

5 Claims, 6 Drawing Sheets

(51) Int. Cl.
*D04H 1/54* (2012.01)
*D06C 3/00* (2006.01)
*A61F 13/513* (2006.01)

(56) References Cited

U.S. PATENT DOCUMENTS

| | | | |
|---|---|---|---|
| 4,469,734 A | 9/1984 | Minto et al. | |
| 4,588,630 A | 5/1986 | Shimalla | |
| 4,965,122 A * | 10/1990 | Morman | 442/328 |
| 5,151,092 A | 9/1992 | Buell et al. | |
| 5,292,239 A | 3/1994 | Zeldin et al. | |
| 5,397,413 A | 3/1995 | Trimble et al. | |
| 5,414,914 A | 5/1995 | Suzuki et al. | |
| 5,470,639 A | 11/1995 | Gessner et al. | |
| 5,518,801 A | 5/1996 | Chappell et al. | |
| 5,628,097 A | 5/1997 | Benson et al. | |
| 5,714,107 A | 2/1998 | Levy et al. | |
| 5,873,868 A * | 2/1999 | Nakahata | 604/383 |
| 5,916,661 A | 6/1999 | Benson et al. | |
| 6,632,504 B1 | 10/2003 | Gillespie et al. | |

FOREIGN PATENT DOCUMENTS

| | | |
|---|---|---|
| WO | WO 96/10979 A1 | 4/1996 |
| WO | WO 97/19662 A1 | 6/1997 |
| WO | WO 01/71080 A1 | 9/2001 |

* cited by examiner

METHOD OF MAKING HIGH-ELONGATION APERTURED NONWOVEN WEB

CROSS REFERENCE TO RELATED APPLICATIONS

This patent application is a divisional application of now abandoned U.S. patent application Ser. No. 09/909,486 filed Jul. 20, 2001, and claims the benefit thereof.

FIELD OF INVENTION

The present invention relates to highly-extensible apertured nonwoven webs and a method of making the same. Apertured nonwoven webs are particularly well suited for use in disposable absorbent articles such as diapers, incontinence briefs, training pants, feminine hygiene garments, and the like.

BACKGROUND OF THE INVENTION

Nonwoven webs formed by nonwoven extrusion processes such as, for example, meltblowing processes and spunbonding processes may be manufactured into products and components of products so inexpensively that the products could be viewed as disposable after only one or a few uses. Representatives of such products include disposable absorbent articles, such as diapers, incontinence briefs, training pants, feminine hygiene garments, and the like.

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art.

A typical absorbent article includes a liquid pervious topsheet, a liquid impervious backsheet joined to the topsheet, and an absorbent core positioned between the topsheet and the backsheet. Nonwoven webs are often used as the topsheet because they are liquid pervious and provide a skin friendly surface. However, in certain uses nonwoven webs do not function all that well as a topsheet as body exudates sometimes hang-up or get caught in the nonwoven web and thus become trapped against the wearer's skin. One solution to the aforementioned problem is to provide apertures in the nonwoven web so that body exudates may readily penetrate through the nonwoven web and into the underlying absorbent core. Unfortunately, certain techniques used to form apertured nonwoven webs are either costly, create an undesirable harsh feeling against the wearer's skin, or are subject to tearing, particularly when the apertured nonwoven web is to be used as a topsheet on a disposable absorbent article.

One economical method of forming apertures in a nonwoven to solve the above-mentioned problems taught in U.S. Pat. No. 5,628,097, entitled Method For Selectively Aperturing a Nonwoven Web, which issued May 13, 1997 to Curro et al.; and, U.S. Pat. No. 5,916,661, entitled Selectively Apertured Nonwoven Web, which issued Jun. 29, 1999 to Curro et al., both of which are hereby incorporated herein by reference. The nonwoven webs taught by both Curro et al. patents have proven to be effective as topsheets in disposable absorbent garments, including disposable diapers. The apertures formed by the processes described are effective for management of higher viscosity body wastes, for example.

Apertured nonwoven webs can be made by several other processes as well, for example by i) slitting and stretching as described in U.S. Pat. No. 5,714,107, entitled Perforated Nonwoven Fabrics; ii) perforating with patterned rolls as in European Patent No. EP-A-0 955 159, entitled Method for Forming Apertured Laminate Web; iii) hydroentangling or hydroaperturing as described in U.S. Pat. No. 5,414,914, entitled Process for Producing Apertured Nonwoven Fabric; and iv) hot needling as described in U.S. Pat. No. 4,469,734, entitled Microfibre Web Products.

The open area and hole size are two important properties of apertured webs for use as a topsheet in a disposable absorbent article. In order to effectively accept viscous body exudates, the open area of each aperture needs to be greater than 1 $mm^2$, preferably greater than 2 $mm^2$ and most preferably greater than 3 $mm^2$. Also, the total open area of the entire topsheet is preferably at least about 15%. Ideally, the apertures, or holes should be circular, or almost circular. However, if the holes are oval shaped, the hole aspect ratio, which is defined as the ratio of the major axis to the minor axis of the oval, should be less than 8, preferably less than 6 and most preferably less than 4.

While producing high quality, economical apertured nonwoven webs, the webs taught by Curro et al., as well as webs made by the other methods listed above suffer from the drawback that with known technology, the webs exhibit a cross-machine direction extensibility that limits their use in certain high-extensible disposable garment products. For example, as disposable absorbent garments are improved, extensibility of the various components becomes more important. In disposable diapers, for example, it is desirable to have extensible chassis components such as the backsheet and the topsheet. Extensible components permit a wider range of unrestricted movement of the wearer, such as a baby. Higher extensibility results in easier application, less restriction of the skin, and higher comfort levels for the wearer.

Current apertured nonwovens typically have essentially the same extensibility of the base, i.e., non-apertured nonwoven. That is, the aperturing process does not improve the extensibility characteristics. Even apertured nonwovens designed specifically for disposable absorbent articles, such as those manufactured according to the teachings of Curro et al., typically have cross-machine direction extensibility of about 50% at a loading of 25 g/in. (25 g/2.54 cm, which is about 10 g/cm) tensile force. That is, an apertured nonwoven web, such as for a diaper topsheet, having a cross-machine direction dimension of 100 cm could elongate in that direction up to about 150 cm under a tensile loading of about 10 g/cm (10 grams per linear centimeter applied to each opposing edge being grasped to put the web in tensile loading) without significant degradation in performance or material integrity.

Certain apertured nonwoven webs may exhibit sufficient extensibility, but, nevertheless, fail to maintain adequate hole size and shape upon extension. For example, apertured nonwoven webs that are made by the slitting and stretching approach can potentially be made extensible by consolidating the slit web, i.e. stretching it in the machine direction to make it neck to a narrower width in cross machine direction. This approach, however, decreases the hole size substantially and will also increase the hole aspect ratio. Another potential approach is to consolidate the web and then slit and stretch it. However, when such a web is stretched in cross machine direction, the web will tend to return to its unnecked state prior to the holes opening up, thus losing the benefit of consolidation. Yet another potential approach may be to consolidate the web and punch holes in it via processes like hot needling. These webs are unsuitable for diaper application as they are not soft. This is because of the thick melt edges that are left behind where the apertures are formed.

Accordingly, it would be desirable to have an apertured nonwoven web that has hole size greater than 2 m², total open area greater than 15% and hole aspect ratio less than 6 and that can, in addition, exhibit cross-direction extensibility greater than about 50% at about 10 g/cm tensile force.

Additionally, it would be desirable to have an apertured nonwoven web suitable for use as a topsheet in a disposable diaper, that can exhibit cross-direction extensibility greater than about 70% at 10 g/cm tensile force.

Further, it would be desirable to have an economical method for making an apertured nonwoven web that can exhibit cross-direction extensibility greater than about 70% at 10 g/cm tensile force.

SUMMARY OF THE INVENTION

In accordance with the present invention there is provided an extensible apertured nonwoven web, and a method for making such an apertured nonwoven web. In one embodiment the method comprises the steps of providing an apertured nonwoven web, incrementally stretching it in a direction substantially parallel to the cross machine direction, and applying tension in the machine direction such that the web width after applying tension is less than the web width after incremental stretching. In another embodiment the method comprises the steps of providing a nonwoven web; weakening the nonwoven web at a plurality of locations to create a plurality of weakened, melt-stabilized locations; applying a first tensioning force to the nonwoven web to cause the nonwoven web to rupture at the plurality of weakened, melt-stabilized locations creating a plurality of apertures in the nonwoven web coincident with the weakened, melt-stabilized locations, incrementally stretching the nonwoven web in a direction substantially parallel to the cross machine direction, and applying tension in the machine direction such that the web width after applying machine direction tension is less than the web width after incremental stretching. An apparatus for producing a web of the present invention by this method is also disclosed.

The extensible apertured nonwoven web produced has a plurality of apertures each having a hole size greater than 2 mm², and a hole aspect ratio less than 6, the nonwoven web having an open area greater than 15% and being capable of at least 70% extension in the cross machine direction at a loading of 10 g/cm.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
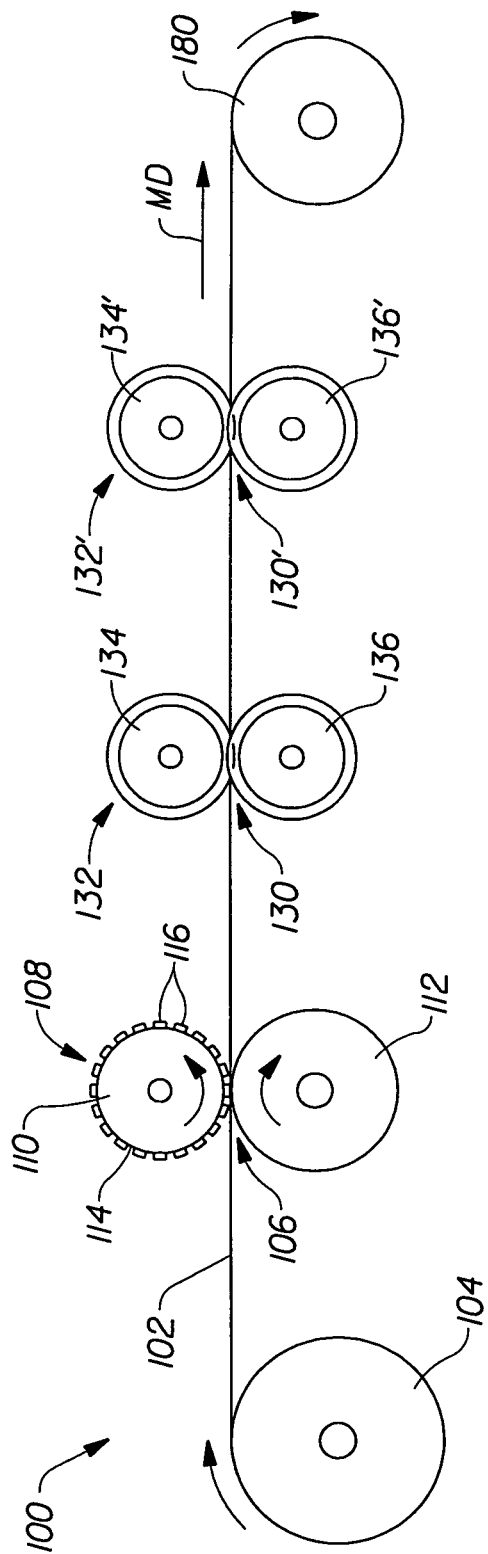
FIG. 1 is a schematic representation of an exemplary process for making a nonwoven web of the present invention.

As used herein, the term "nonwoven web" is used in its normal sense, and specifically refers to a web that has a structure of individual fibers or threads which are interlaid, but not in any regular, repeating manner. Nonwoven webs can be formed by a variety of known processes, such as, for example, meltblowing processes, spunbonding processes and bonded carded web processes. The nonwoven web, without apertures and prior to processing as disclosed herein, is also referred to as the "precursor web."

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1.0) cm sample of a material which is elongatable to at least 1.60 cm, and which, upon being elongated to 1.60 cm and released, will recover to a length of not more than 1.27 cm. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force.

As used herein, the term "nonelastic" refers to any material which does not fall within the definition of "elastic" above.

As used herein, the term "extensible" refers to any material which, upon application of a biasing force, is elongatable, at least about 50% without offering a significant resistance force (less than 10 g/cm) or experiencing catastrophic failure. Catastrophic failure includes substantial tearing, fracturing, rupturing, or other failure in tension such that, if tested in a standard tensile tester, the failure would result in a sudden significant reduction in measured tensile force. As used herein, the term "highly extensible" refers to any material which, upon application of a biasing force, is elongatable, at least about 70%, more preferably at least about 100%, and even more preferably about 120% without without offering a significant resistance force (less than 10 g/cm) or experiencing catastrophic failure.

As used herein, the term "melt-stabilized" refers to portions of a nonwoven web which have been subjected to localized heating and/or localized pressure to substantially consolidate the fibers of the nonwoven web into a stabilized film-like form.

As used herein, unless otherwise specified, all composition percentages are weight percentages.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

As used herein the term "hole size" refers to the average size of the open area of a single aperture, measured in units of area, for example, square millimeters.

As used herein the term "open area" refers to the percentage of the total area of a web that has apertures.

As used herein the term "hole aspect ratio" is the ratio of the major axis to the minor axis of a single aperture that is approximately oval shaped.

By "cross-machine direction" is meant the direction corresponding to the cross-machine direction of the web during web production, which is orthogonal to the "machine-direction". Thus, during web production, the direction corresponding to the linear direction of web production, i.e., the "length" of the web, is the machine-direction. The direction transverse to the machine-direction, i.e., the "width" of the web, is the cross-machine direction as used herein.

For typical diapers produced on high speed diaper equipment, the cross-machine direction of the component web materials corresponds to a direction generally parallel to a transverse centerline of the finished diaper, as described more fully herein. It is this direction in which improvements in diaper extensibility are desired.

A typical diaper comprises a containment assembly, commonly referred to as a "chassis" comprising a liquid pervious topsheet and a liquid impervious backsheet joined to the topsheet. An absorbent core is positioned between the topsheet and the backsheet. The diaper preferably further comprises other components as known in the art, such as elasticized side panels; elasticized leg cuffs; elasticized waistbands; and a fastening system preferably comprising a pair of securement members (e.g., tape tabs or mechanical fastener members) and a landing member.

A diaper also has two centerlines, a longitudinal centerline and a transverse centerline. The term "longitudinal", as used herein, refers to a line, axis, or direction in the plane of the diaper that is generally aligned with (e.g. approximately parallel with) a vertical plane which bisects a standing wearer into left and right halves when the diaper is worn. The terms "transverse" and "lateral", as used herein, are interchangeable and refer to a line, axis or direction which lies within the plane of the diaper that is generally perpendicular to the longitudinal direction (which divides the wearer into front and back body halves).

While the topsheet, the backsheet, and the absorbent core may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The topsheet can be made from a web of the present invention, thereby being apertured so as to allow viscous body fluids, like runny and pasty BM and menses, to go through and get stored in the layers beneath. Key properties of the apertured topsheet (ATS) are open area, hole size, and hole aspect ratio. In a preferred embodiment, the open area is greater than about 15% and the hole size is greater than about 2 mm$^2$. In some instances minimum and/or maximum hole size is important, but, unless noted otherwise herein, hole size refers to average hole size. Ideally, the holes should be circular in shape and relatively consistent in size, such that the standard deviation of the average hole size is very small. Non-round, for example oval shaped, holes would also be functional provided the hole aspect ratio, which is defined as the ratio of the major axis to the minor axis of the ellipse, is not too large. For holes having a major axis within the ranges disclosed herein, e.g., from 2-4 mm, the hole aspect ratio is preferably less than about 6.

The topsheet made according to the the present invention comprises a highly extensible apertured nonwoven web. By highly extensible is meant that the apertured nonwoven web of the present invention exhibits cross-direction extensibility at a load of about 10 g/cm of at least about 70%, more preferably at least about 100%, and even more preferably about 120%. By way of comparison, webs produced as taught by Curro et al. in the above-mentioned U.S. patents exhibit cross-direction extensibility of about 50% at about 10 g/cm loading.

Referring to FIG. 1 there is schematically illustrated at 100 a process for producing a highly extensible apertured nonwoven web suitable for use as a topsheet on a disposable absorbent article.

According to the present invention, a precursor nonwoven web 102 is supplied as the starting material. The precursor nonwoven web 102 can be supplied as discrete webs, e.g., sheets, patches, etc., of material for batching processing. For commercial processing, however, precursor nonwoven web is supplied as roll stock, and, as such it can be considered as having a finite width and an infinite length. In this context, the length is measured in the machine direction (MD) which is the direction of web travel during processing. Likewise, the width is measured in the cross machine (CD) direction.

The nonwoven material 102 may be formed by known nonwoven extrusion processes, such as, for example, known meltblowing processes or known spunbonding processes, and passed directly through the nip 106 without first being bonded and/or stored on a supply roll.

The nonwoven web 102 may be extensible, elastic, or nonelastic, as long as it can be processed by the methods described herein and retain the properties described herein. That is, a great many types of webs can be processed by the method of the present invention, but not all nonwoven webs can be so processed. As shown more fully below, a correlation has been found between the CD peak tensile elongation properties of a precursor web and processability of such a web into a web of the present invention. In general, to obtain a high-elongation apertured web of the present invention, the precursor nonwoven web material should exhibit a peak CD tensile elongation of at least about 150%, more preferably about 175%, and most preferably about 200%. "Peak CD tensile elongation" refers to the highest force exhibited in a standard tensile test. Tensile properties of the precursor webs of the present invention are measured using Instron or MTS equipment, or the like, using standard tensile test methodologies. In general, the sample width tested was one inch (2.54 cm), gage length was two inches (5.08 cm), crosshead speed was two inches per minute (5.08 cm/min), and the slack preload was one gram.

As long as it exhibits the above-described CD peak tensile elongation properties, precursor nonwoven web 102 may be a spunbonded web, a meltblown web, or a bonded carded web. If the nonwoven web is a web of meltblown fibers, it may include meltblown microfibers. The nonwoven web 102 may be made of fiber forming polymers such as, for example, polyolefins. Exemplary polyolefins include one or more of polypropylene, polyethylene, ethylene copolymers, propylene copolymers, and butene copolymers. In a preferred embodiment, the precursor nonwoven web 102 (prior to processing by the method of the present invention), has a basis weight of between 20 grams per square meter (gsm) and 70 gsm, more preferably between about 30 gsm and 60 gsm. A currently preferred basis weight for diaper topsheet applications is between about 40 and 50 gsm.

Likewise, in another embodiment, the precursor nonwoven web 102 may be a multilayer material having, for example, at least one layer of a spunbonded web joined to at least one layer of a meltblown web, a bonded carded web, or other suitable material. For example, the precursor nonwoven web 102 may be a multilayer web having two layers of spunbonded polypropylene, each having a basis weight from about 20 to about 60 grams per square meter (gsm).

The precursor nonwoven web 102 may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly (vinyl chloride); polyester; polyurethane; compatible polymers; compatible copolymers; and blends, laminates and/or combinations thereof.

The precursor nonwoven web 102 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers and particles occurs prior to collection of the fibers.

The nonwoven web of fibers should be joined by bonding to form a coherent web structure suitable for processing, such as from rollstock. Suitable bonding techniques include, but are not limited to, chemical bonding; thermobonding, such as point calendaring; hydroentangling; and needling.

Precursor nonwoven web 102 is unwound from a supply roll 104 and travels in a direction indicated by the arrows (i.e., the machine direction) associated therewith as the supply roll 104 rotates in the direction indicated by the arrows associated therewith. The nonwoven material 102 passes through a nip 106 of the web weakening roller arrangement 108 formed by rollers 110 and 112.

Figure 2:
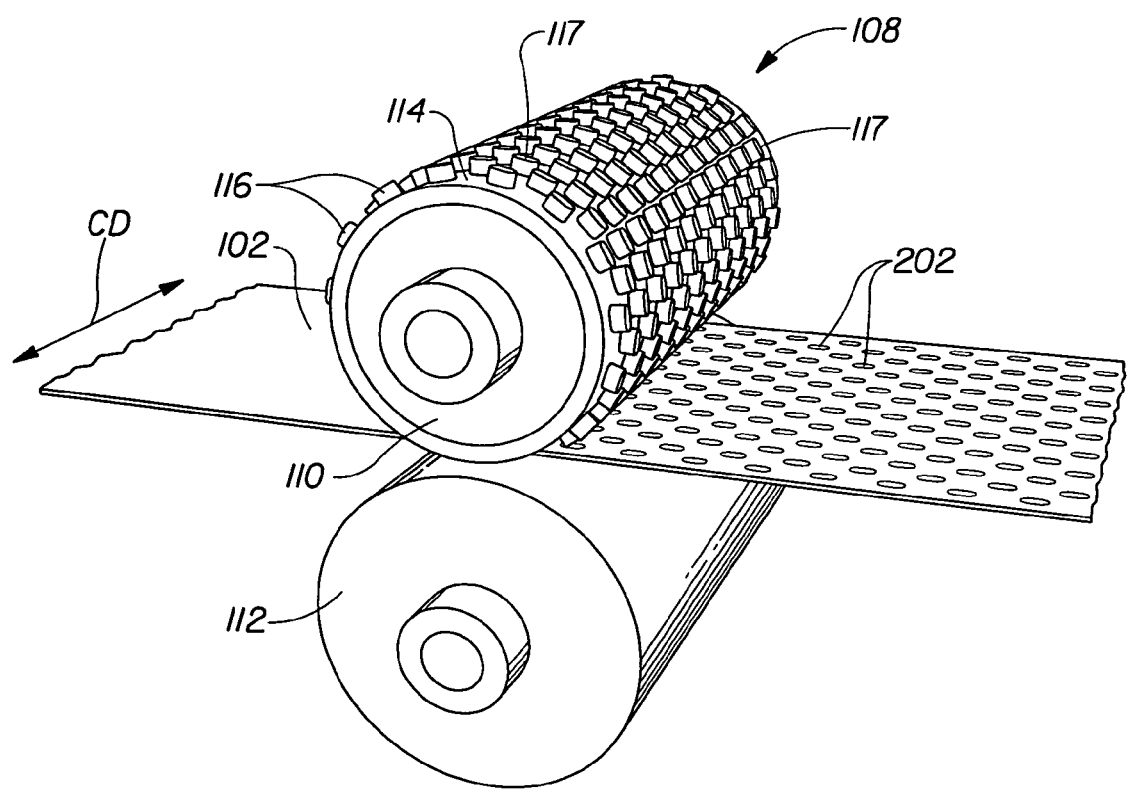
FIG. 2 is an enlarged perspective illustration of a web weakening arrangement of the present invention.

Referring to FIG. 2, the nonwoven web weakening roller arrangement 108 comprises a patterned calendar roller 110 and a smooth anvil roller 112. One or both of the patterned calendar roller 110 and the smooth anvil roller 112 may be heated and the pressure between the two rollers may be adjusted by well known means to provide the desired temperature, if any, and pressure to concurrently weaken and melt-stabilize the nonwoven web 102 at a plurality of locations.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to precipitate a weakened, melt-stabilized location in the nonwoven web 102 to effect a predetermined pattern of weakened, melt-stabilized locations in the nonwoven web 102. As shown in FIG. 2, patterned calendar roller 110 has a repeating pattern of protuberances 116 which extend about the entire circumference of surface 114. Alternatively, the protuberances 116 may extend around a portion, or portions of the circumference of surface 114.

Figure 3:
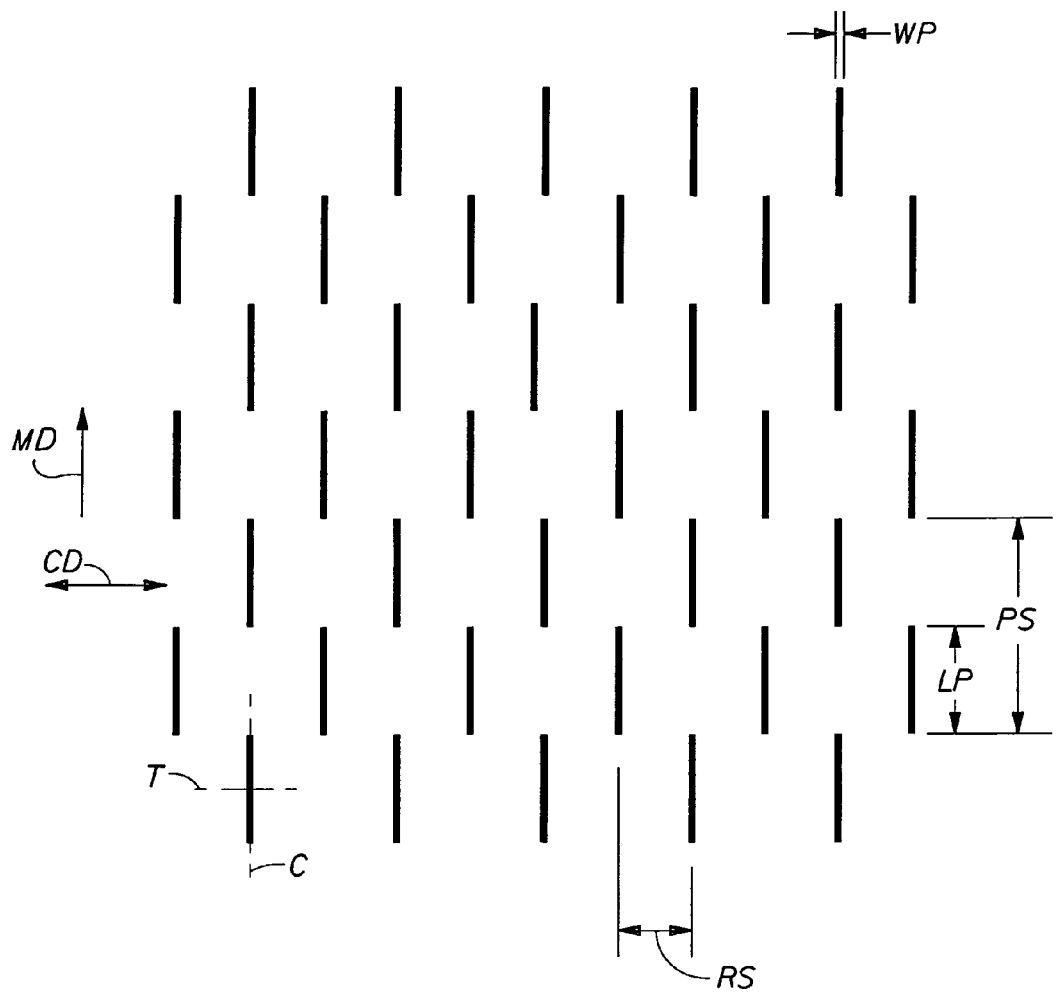
FIG. 3 is a schematic representation of a pattern for the protuberances of weakening arrangement of the present invention.

A suitable pattern for patterned calendar roller 110 is shown schematically in plan view in FIG. 3. Because the protuberances 116 have a one-to-one correspondence to the pattern of melt-stabilized locations, FIG. 3 can also be considered as illustrating a typical pattern of melt-stabilized locations on a calendared nonwoven web according to the present invention. As shown, the protuberances can be in a regular pattern of staggered rows or columns. The pattern shown is a regular repeating pattern of staggered protuberances, generally in rows, each separated by a row spacing, RS, of between about 0.030 inches (0.76 mm) and about 0.200 inches (5.08 mm). In a preferred embodiment, row spacing RS is about 0.060 inches (1.52 mm). The protuberances can be spaced apart within a column by a protuberance spacing, PS generally equal to the protuberance length, LP, which in one embodiment is 0.150 inches (3.81 mm). But the spacing and pattern can be varied in multiple ways depending on the end product desired.

The protuberances have a longitudinal centerline, C, that is oriented generally parallel to the machine direction, MD, of the web material. Likewise, each protuberance has a transverse centerline, T, generally orthogonal to the longitudinal centerline. The longitudinal dimension LP of each protuberance 116 corresponds to the dimension measured parallel to the longitudinal centerline C, and is much longer than the transverse dimension WP (likewise corresponding to the dimension measured parallel to the transverse centerline T), thereby resulting in the protuberances, and the corresponding melt-stabilized locations, having a relatively high aspect ratio (i.e., LP/WP). The aspect ratio is preferably greater than 10, more preferably 15. The height of the protuberances, i.e., the distance the protuberances extend from the circular cylindrical surface 114, should be selected according to the thickness of the nonwoven web being melt-stabilized. In general, the height dimension should be greater than the maximum thickness of the web during the calendaring process, so that adequate melt-stabilizing can be accomplished.

In general, it has been shown that by increasing the aspect ratio of the protuberances, the corresponding aspect ratio of the melt-stabilized locations contributes to the overall CD extensibility of the finished highly extensible web of the present invention. The increased aspect ratio contributes to a geometric expansion advantage. However, it has been discovered that, for webs having suitable open area and hole size for use as topsheets in disposable diapers, the advantage only represents about 10-20% extra elongation in the CD. While the parameter of aspect ratio of the melt-stabilized locations alone could be sufficient to create highly extensible apertured webs, it is believed that such webs would result in an apertured web wherein the apertures have an unacceptably high hole aspect ratio (major dimension/minor dimension of the resulting apertures) for the applications of interest, including use in disposable absorbent articles.

The protuberances 116 are preferably truncated conical shapes which extend radially outwardly from surface 114 and which can have somewhat elliptical distal end surfaces 117. Although it is not intended to thereby limit the scope of the present invention to protuberances of only this configuration. The roller 110 is finished so that all of the end surfaces 117 lie in an imaginary right circular cylinder which is coaxial with respect to the axis of rotation of roller 110.

Although the protuberances 116 can be disposed in a regular predetermined pattern of rows and columns as shown in FIG. 3, it is not intended to thereby limit the scope of the present invention to the pattern of protuberances of shown. The protuberances may be disposed in any predetermined pattern about patterned calendar roll 110. In particular, it is believed that "fishbone" or "herringbone" patterns would be useful for the present invention. Typically, the longitudinal axis of the melt stabilized regions is at an angle of 45 degrees or less off of the machine direction of the nonwoven web. These webs are incrementally stretched in the cross machine direction in order to open up the apertures. If the longitudinal axis of the melt stabilized regions is at an angle greater than 45 degres off of the machine direction, incremental stretching needs to be done in the machine direction. Anvil roller 112, is preferably a smooth surfaced, right circular cylinder of steel.

Figure 4:
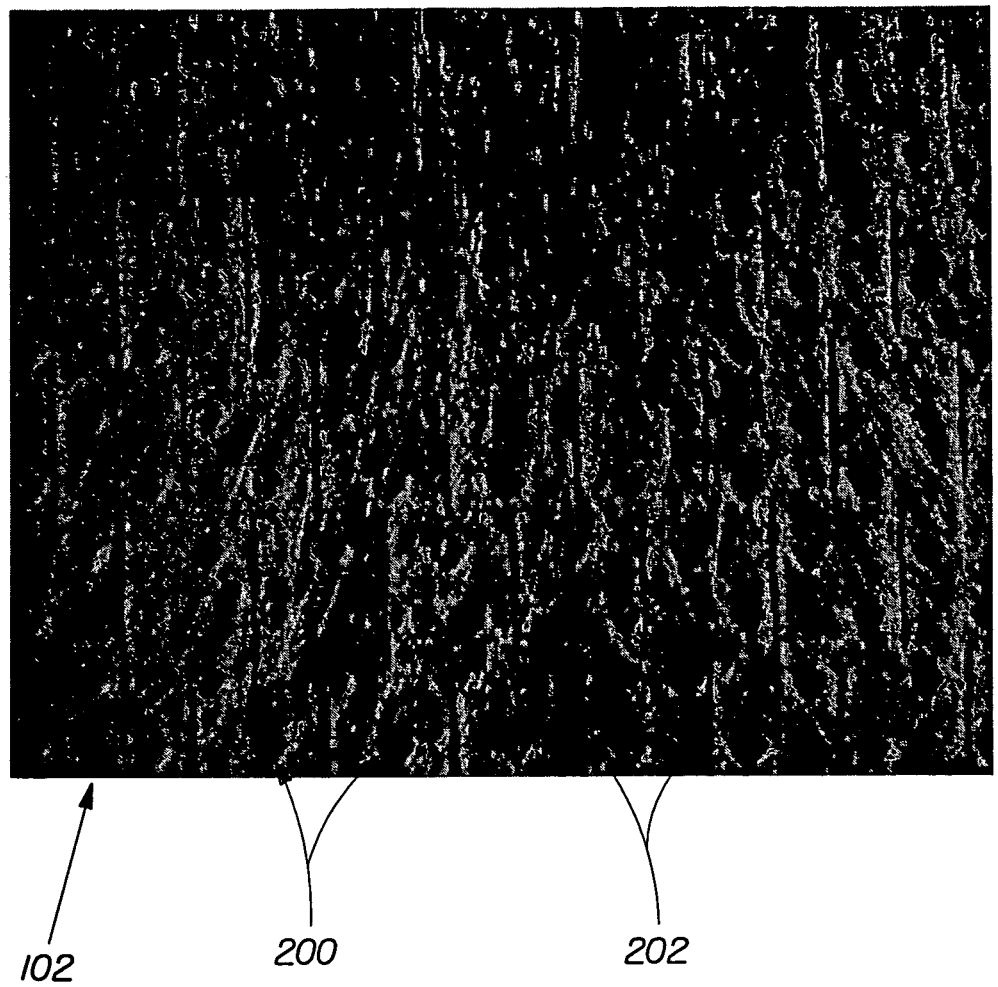
FIG. 4 is an enlarged plan view photograph of a nonwoven web of the present invention after the nonwoven web has been weakened at a plurality of locations.

FIG. 4 is a photograph of the nonwoven web 102 after having passed through the weakening roller arrangement 108, and prior to passing through the nip 130 of the first incremental stretching system 132. As can be seen in the photograph, the nonwoven web 102 includes a plurality of weakened, melt-stabilized locations 202. Weakened, melt-stabilized locations 202 correspond to the pattern of protuberances 116 extending from the surface 114 of patterned calendar roller 110. As seen in FIG. 4, the nonwoven web 102 also includes coherent web forming point calendered bonds 200 which serve to maintain the structural integrity of the nonwoven web 102.

From the weakening roller arrangement 108, the nonwoven web 102 can be stretched in the CD direction by means of a tensioning force to rupture the plurality of weakened, melt-stabilized locations, thereby creating a plurality of apertures in the nonwoven web coincident with the plurality of weakened, melt-stabilized locations. Various tensioning means can be utilized, such as tentoring, however in a preferred embodiment, uniform tensioning throughout the web is achieved by passing the nonwoven web through a nip 130 formed by a first incremental stretching system 132 employing opposed pressure applicators having three-dimensional surfaces which at least to a degree are complementary to one another.

Figure 5:
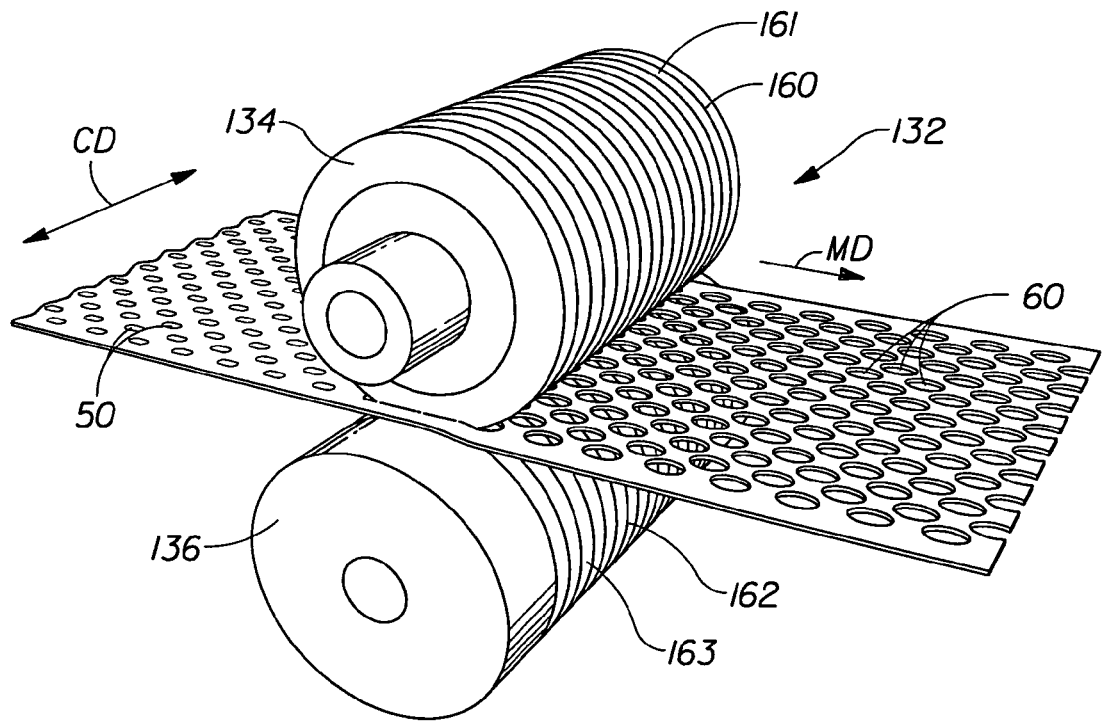
FIG. 5 is a perspective view of an apparatus for stretching a nonwoven web of the present invention.
Figure 6:
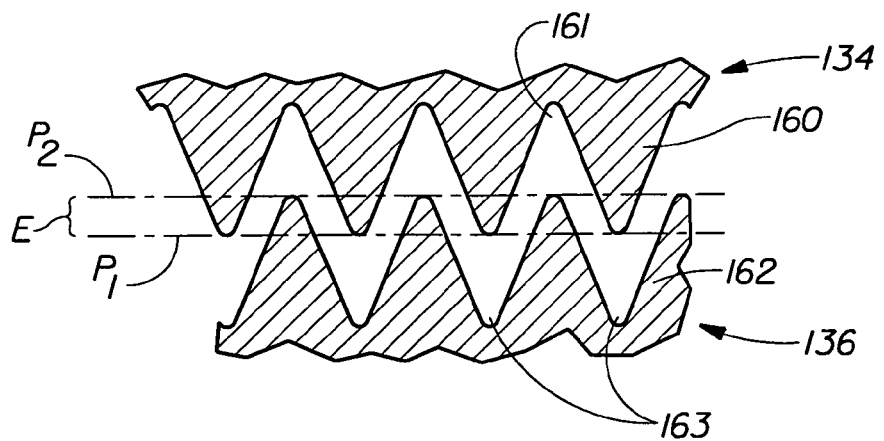
FIG. 6 is an enlarged illustration showing details of the incremental stretching system of the present invention.

Referring now to FIG. 5, there is shown a perspective view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. The teeth of each roller are generally triangular-shaped, as shown in FIG. 6. The apex of the teeth may be slightly rounded, if desired for certain effects in the finished web.

With reference to FIG. 6, which shows a portion of the intermeshing of the teeth 160 and 162 of rollers 134 and 136, respectively, the term "pitch" refers to the distance between the apexes of adjacent teeth. The pitch can be between about 0.02 to about 0.30 inches (0.51-7.62 mm), and is preferably between about 0.05 and about 0.15 inches (1.27-3.81 mm). The height (or depth) of the teeth is measured from the base of the tooth to the apex of the tooth, and is preferably equal for all teeth. The height of the teeth can be between about 0.10 inches (2.54 mm) and 0.90 inches (22.9 mm), and is preferably about 0.25 inches (6.35 mm) and 0.50 inches (12.7 mm).

The teeth 160 in one roll can be offset by one-half the pitch from the teeth 162 in the other roll, such that the teeth of one roll (e.g., teeth 160) mesh in the valley (e.g., valley 163) between teeth in the mating roll. The offset permits intermeshing of the two rollers when the rollers are "engaged" or in an intermeshing, operative position relative to one another. In a preferred embodiment, the teeth of the respective rollers are only partially intermeshing. The degree to which the teeth on the opposing rolls intermesh is referred to herein as the "depth of engagement" or "DOE" of the teeth. As shown in FIG. 6, the DOE, E, is the distance between a position designated by plane P1 where the apexes of the teeth on the respective rolls are in the same plane (0% engagement) to a position designated by plane P2 where the apexes of the teeth of one roll extend inward beyond the plane P1 toward the valley on the opposing roll. The optimum or effective DOE for particular laminate webs is dependent upon the height and the pitch of the teeth and the materials of the web.

In other embodiments the teeth of the mating rolls need not be aligned with the valleys of the opposing rolls. That is, the teeth may be out of phase with the valleys to some degree, ranging from slightly offset to greatly offset.

As the nonwoven web 102 having weakened, melt-stabilized locations 202 passes through the incremental stretching system 132 the nonwoven web 102 is subjected to tensioning in the CD direction causing the nonwoven web 102 to be extended in the CD direction. The tensioning force placed on the nonwoven web 102 can be adjusted by varying the pitch, DOE, or teeth size, such that the incremental stretching is sufficient to cause the weakened, melt-stabilized locations 202 to rupture creating a plurality of apertures 204 coincident with the weakened melt-stabilized locations 202 in the nonwoven web 102. However, the bonds 200 of the precursor nonwoven web 102 do not rupture during tensioning, thereby maintaining the nonwoven web in a coherent condition even as the weakened, melt-stabilized locations rupture.

After passing through the first incremental stretching system 132, the nonwoven web has width greater than the width of the precursor web, apertures in the regions where the melt-stabilized regions ruptured, and increased extensibility in the cross-machine direction, CD. The actual width in the CD direction depends on the amount of tension applied to the web when it exits the incremental stretching system 132. As expected, narrowing, and even necking of the web can be achieved by increasing the tension in the MD sufficiently. The extension properties described herein are for incrementally stretched webs with little or no tension applied in the MD. At this stage, for nonwovens of suitable basis weight and composition as typically utilized as topsheets in disposable diapers, and having a hole size greater than 2 mm$^2$, and an open area of at least 15%, the elongation at 10 g/cm loading is only about 40-50%. After extension of about 40-50%, the nonwoven web at this stage of processing offers substantial resistance to further tensile loading and, in some cases, begins to tear, shred, or otherwise lose structural integrity.

Figure 7:
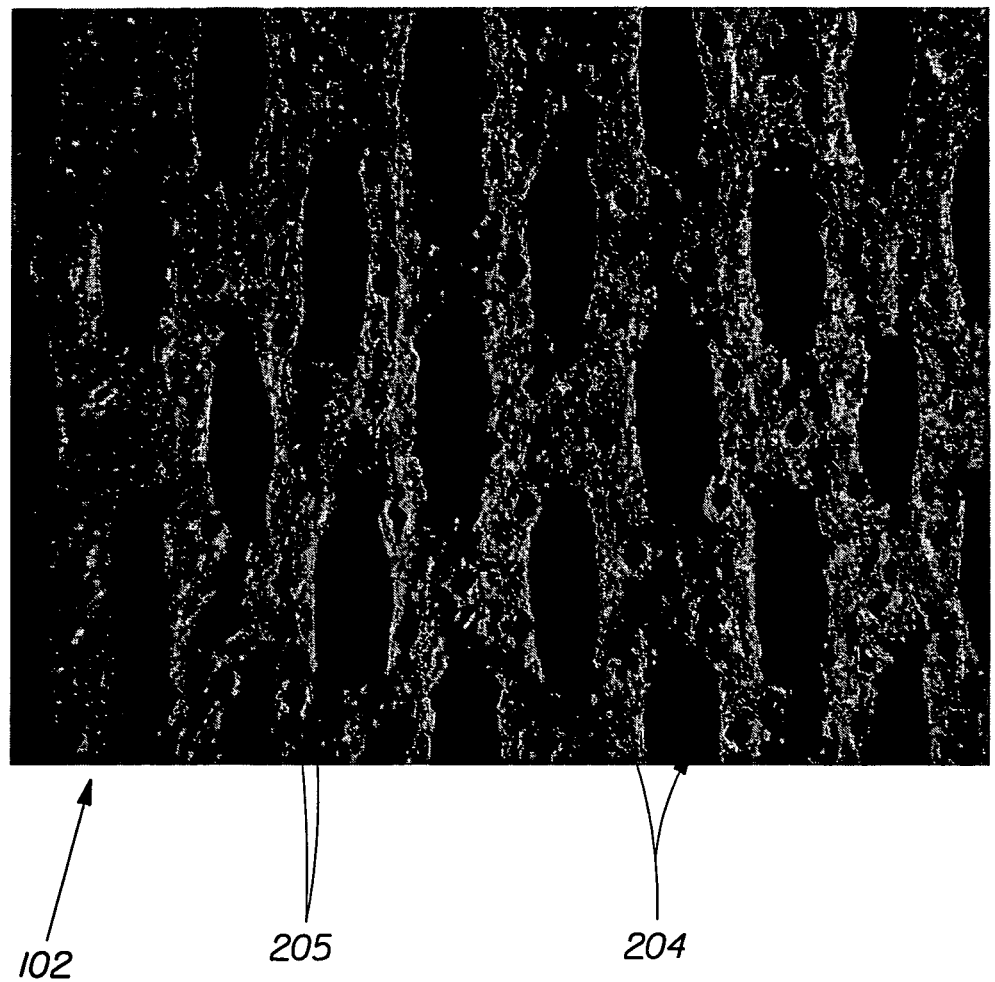
FIG. 7 is an enlarged plan view photograph of a nonwoven web of the present invention after tension has been applied to rupture the nonwoven web at the weakened locations to create apertures in the nonwoven.

Referring now to FIG. 7 there is shown a photograph of the nonwoven web 102 after having been subjected to the tensioning force applied by the incremental stretching system 132. As can be seen in the photograph, the nonwoven web 102 now includes a plurality of apertures 204 which are coincident with the weakened, melt-stabilized locations 202 of the nonwoven web shown in FIG. 4. A portion of the circumferential edges of apertures 204 include remnants 205 of the melt-stabilized locations 202. It is believed that the remnants 205 help to resist further tearing of the nonwoven web particularly when the nonwoven web is used as a topsheet on a disposable absorbent article.

Other exemplary structures of incremental stretching mechanisms suitable for incrementally stretching or tensioning the nonwoven web are described in U.S. Pat. No. 5,518,801 issued to Chappell et al. on May 21, 1996, and hereby incorporated herein by reference.

Newer diaper designs that require higher extensibility of components to facilitate better fit and comfort require that the material for use as the topsheet have at least 70% extension at about 10 g/cm loading. It is important to distinguish between pure extension, and extension under a specified loading, especially a relatively low loading such as about 10 g/cm. For disposable absorbent articles, including diapers, it is important that the extension be available for body movements under low tension and also for ease of application. Low force extension contributes to a feeling of comfort, fit, and softness. For example, when fit about a baby's buttocks regions, it is important that the diaper components substantially freely extend upon movements such as sitting, bending, or twisting. Thus, the diaper does not chaff, rub, or pull on the baby's skin, causing discomfort and skin irritation. The same considerations apply to adult garments, including catamenials, incontinence garments, and the like.

Therefore, to make a highly extensible topsheet, after passing through the first incremental stretching system 132, the nonwoven web is passed through an additional, second incremental stretching system 132'. During the second incremental stretching, the web width is substantially increased. By applying tension in the machine direction, the web width is decreased to about the same level as it was prior to the second incremental stretching. In this process, it is this second incremental stretching step followed by application of MD tension that produces the apertured nonwovens having the requisite extensibility characteristics of the claimed invention. The processing parameters, equipment set up, and related methodologies for the second incremental stretching system 132' can be, and preferably are, substantially identical to first incremental stretching system 132, and therefore, a description for each "prime number" counterpart of first incremental stretching system 132 will not be repeated here. In a preferred embodiment, the nonwoven web of the present invention is processed in the second incremental stretching system 132' in the same manner, and with respect to the same methodologies as described above with respect to incremental stretching system 132. However, for certain other embodiments second incremental stretching system 132' can differ significantly in certain respects, for example, in the pitch and depth of engagement of the mating rollers.

The purpose of the second incremental stretching system 132' is to put further extension potential into the nonwoven web in the form of additional incremental stretching of the previously incrementally-stretched web. By "extension potential" is meant that after incrementally stretching and necking according to the process described herein, the nonwoven web can be, and preferably is, essentially the same width in the cross machine direction as before the second stretching step, yet it is able to extend substantially beyond its original width in the cross machine direction. This is believed to be partly due to the accordian-like, or fan-folded, pleating induced in the web during incremental stretching. It is believed that this additional incremental stretching can only be achieved, as stated above, when the precursor web exhibits a certain minimum extensibility. Otherwise, the second incremental stretching step simply shreds the nonwoven web. By controlling the tensions of the web as it exits the incremental stretching apparatus, the width of the finished nonwoven web can be maintained at a predetermined dimension, with a corresponding extension potential of over 100% at low extension forces.

As noted above, the additional incremental stretching of the nonwoven web by the method of the present invention may stretch the nonwoven beyond the limit of which the constituent fibers and bonds are able to withstand structural integrity. Therefore, the precurser nonwoven web for the present invention must have sufficient structural properties to withstand such additional incremental stretching. Such precursers nonwoven webs have been developed for the present invention, embodiments of which are described herein, including in Table 1 of the Examples section below.

Incremental stretching via the apparatus described herein is preferred due to its ability to uniformly stretch the web across its width. However, the second stretching step could be achieved by other stretching means, such as tentoring, with a subsequent "consolidation" step that would put the post-tentored web in machine direction tension thereby necking the web down to the pre-tentoring width.

Additionally, if desired, the incremental stretching steps described herein can be performed at elevated temperatures. For example, one or both of the incremental stretching rollers could be heated. Utilizing heat in the stretching step serves to soften the nonwoven web, and aids in extending the fibers without breaking.

The nonwoven web 102 is preferably taken up on wind-up roll 180 and stored. Alternatively, the nonwoven web 102 may be fed directly to a production line where it is used to form a topsheet on a disposable absorbent article.

Both the first and second incremental stretching can either be done off-line or on-line. Furthermore, the incremental stretching can either be done over the entire area of the web or only in certain regions. For example, the second incremental stretching can be done only in a region corresponding to the back portion of a diaper where high extensibility is desired.

With certain highly extensible precursor nonwoven webs, it may be possible to achieve a highly extensible apertured nonwoven web with just one incremental stretching step instead of two, followed by limited spreading and MD tensioning. In this approach, the web having the above-mentioned melt weakened regions can be incrementally stretched to at a relatively high depth of engagement (DOE), after which MD tension is applied to achieve the desired open area, hole size, aspect ratio, and CD extensibility.

In another embodiment, an extensible apertured nonwoven web can be made by first aperturing a nonwoven web by other known methods, such as by slitting and stretching, perforating with patterned rolls, hydroentangling or hydroaperturing, or hot needling, subjecting the apertured nonwoven material to at least one incremental stretching step as described above, and then applying tension in the machine direction to reduce the web width (i.e., consolidate the web) as described above. In this manner, the requisite extensiblility can be imparted to an apertured nonwoven web to make it a highy extensible nonwoven web, the web having at least 70% extension at about 10 g/cm loading. In an alternative process for forming a highly-extensible nonwoven web of the present invention, the nonwoven web weakening arrangement can comprise an ultrasonic transducer and an anvil cylinder instead of thermal point bonding protuberances. As the nonwoven material is forwarded between the ultrasonic transducer and the anvil cylinder it is subjected to ultrasonic vibrational energy whereupon predetermined pattern locations of the nonwoven web are weakened and melt-stabilized. A suitable transducer is described in the aforementioned U.S. Pat. No. 5,628,097 patent. As disclosed above, in this process, after passing through the first incremental stretching system the nonwoven web is passed through an additional, second incremental stretching system that produces the apertured nonwovens having the requisite extensibility characteristics of the claimed invention.

EXAMPLES

Table 1 lists mechanical properties of several nonwoven webs processed by the method of the present invention. As shown, certain precursor nonwoven materials are not suitable for such processing. The samples disclosed in these Examples which can be processed into highly-extensible apertured nonwovens are shown are meant to be illustrative of possible structures, and are not meant to be limiting to any particular material or structure.

All the samples shown in Table 1 were processed as described below. For samples 1, 2, 3, 5 and 6 web weakening was achieved by thermal bonding of rollstock precursor nonwovens using web weakening roller arrangement 108 in a continuous process. For sample 4 web weakening was achieved ultrasonically on handsheets of the precursor nonwovens. For the samples that were thermally bonded, the line speed through the web weakening roller arrangement 108 was about 250 feet per minute (about 75 meters per minute), but the line speed is not considered critical to the operation of the method. The patterned calendaring pressure, i.e., nip pressure, was about 700 psig (4823 kPa) for all the samples, but the pressure can be varied as desired as long as sufficient melt stabilization is achieved. Line speed and nip pressures are considered to be variable, depending on the materials being processed, and suitable variations are within the abilities of one skilled in the art without undue experimentation. The patterned calendar roller 110 was configured with pattern elements 116 having a row spacing RS (or pitch) of 0.060 inches (1.52 mm), a protuberance width, WP, of 0.010 inches (0.25 mm), and a protuberance length, LP, of either 0.100 inches (2.54 mm) (Samples 1 and 2) or 0.150 inches (3.81 mm) (Samples 3-6).

To form the extensible apertured nonwoven webs shown in Table 1 below (except for ultrasonically-bonded sample 4), after the patterned calendar roller, the thermally bonded laminate was processed by the first and second incremental stretching processes as described above with reference to FIG. 1. For these samples the incremental stretching roller pitch was 0.060" (1.52 mm) and the line speed was 250 fpm (about 75 meters per minute). Depth of engagement ("DOE") was varied as shown to achieve the requisite extensibility without destroying the web. Sample 4 was processed using mating flat plate variants of incremental stretching rollers, with similar pitches, DOE, as shown.

Samples 1a and 1b, described in the Table as "50/50 PE/PP bico SB Lurgi process", are spunbond webs comprising 50% polyethylene sheath/50% polypropylene core bicomponent fibers having a fiber denier from about 3-5. The nonwovens are available from BBA, Simpsonville, S.C., USA, and are made via a standard Lurgi process, as known in the art. Peak elongations are typically lower than 150% measured by standard tensile testing methods (e.g., Instron, MTS, etc.) with a one inch sample width, one inch gage length, 10 inches/minute crosshead speed, and a slack preload of one gram.

Samples 2a and 2b described in the Table as "50/50 PE/PP bico SB Slot-draw Process" are spunbond webs comprising 50% polyethylene sheath/50% polypropylene core bicomponent fibers having a fiber denier from about 4-6. These precursor nonwovens are available from BBA, Simpsonville, S.C., USA, and are made via a BBA slot drawing process to have relatively high CD peak tensile elongation. Peak elongations are typically greater than 250%, measured by standard tensile testing methods (e.g., Instron, MTS, etc.) with a one inch sample width, one inch gage length, 10 inches/minute crosshead speed, and a slack preload of one gram. These precursor webs are believed to be made according to one or more of the following U.S. Pat. Nos. 5,292,239, 5,470,639, and/or 5,397,413. Samples 3a and 3b were also made using the same slot draw process. However, it is believed that, due to variations in the slot drawing parameters, as set by BBA during manufacture, the CD peak elongation of this precursor nonwoven was lower.

Samples 4a and 4b were made with two layers of precursor nonwovens: the top layer was an 80/20% PE/PP bico spunbond and the lower layer was a 50/50% PE/PP bico spunbond. Both of these precursor nonwovens were made using the slot draw process described above and exhibited CD peak elongations of about 150 and 325% respectively.

Samples 5a and 5b were made from a spunbond nonwoven made with a polypropylene copolymer. This nonwoven, obtained from BBA under the name Softspan 200 exhibited a CD peak elongation of 190%

The 50/50% PE/PP bico SB Lurgi process spunbond that was used for making samples 6a and 6b was similar in chemistry to the precursor web that was used to make samples 1a and 1b, but was processed by BBA so as to have higher CD peak elongation. The higher CD peak elongation enabled this web to be processed into an extensible apertured topsheet with the added variation of using longer bond pattern length (bond length=3.81 mm). Without being bound by theory, it is believed that this bond length is near the limit for effective webs of the present invention for use as topsheets in absorbent garments, due to the resulting aperture size.

The open area, hole size, and hole aspect ratio are indications of the usefulness of the webs for use as topsheets in absorbent garments. In particular, it is desired that hole size and open area are sufficient to permit viscous bodily waste to pass through. However, to function as an effective topsheet, it should also be effective as a barrier between the wearer's skin and the absorbent core of the garment. Thus, the webs of the present invention for use as a topsheet exhibit an acceptable balance of sufficient open area, hole size and hole aspect ratio for use as a topsheet in a disposable absorbent article.

The open area, hole size, and hole aspect ratio are are measured using an optical microscope equipped with a digital camera and an image analysis system. The microscope is a Zeiss SV8 stereoscope (Zeiss Inc., New York, N.Y.) with a 0.5× condenser lens. Since the apertures are fairly large, the magnification needs to be low. Typically, the magnification is low enough to get at least 15 apertures in the field of view. For samples with smaller apertures, there could even be as many as 50 apertures in the field of view. The sample is illuminated from the sides and bottom.

The image is captured by a Sony DKC-ST5 digital camera (Sony Corp., Japan) and the image analysis is done using Image-Pro Plus software (version 4.1.0.2 from Media Cybernetics. The threshold for aperture size is set at 0.4 mm². When measuring hole size and hole aspect ratio, all partial holes, i.e. holes that are only partially in the area of interest, need to be excluded. On the other hand, these partial holes have to be included for open area measurements. The Image-Pro Plus software gives average hole size and hole aspect ratio. Sometimes, the image analysis software may pick up small holes in areas where the nonwoven basis weight is low and/or if the lighting is less than optimal. These holes need to be excluded from all measurements as they would significantly lower the average hole size.

Tensile properties of the apertured webs of the present invention are measured using Instron or MTS equipment using standard tensile test methodologies. For the results shown in Table 1, the sample width was one inch (2.54 cm), gage length was two inches (5.08 cm), crosshead speed was two inches per minute (5.08 cm/min), and the slack preload was zero gram. It is necessary to set the slack preload to zero grams for the apertured webs, since a large part of the extension in these extensible webs occurs at low force that is close to zero grams. Since the incrementally-stretched webs of the present invention have a fluted or mildly corrugated shape, it is important to mark the two-inch gage length on the nonwoven when it is still on the roll, or otherwise in its finished, consolidated width. Once off the roll, some the samples may stretch somewhat in the cross direction, even before applying any tension.

TABLE 1

Samples of processed materials

| | | Precursor Nonwoven | | | Process Conditions | | Apertured Nonwoven | | | | | |
|---|---|---|---|---|---|---|---|---|---|---|---|---|
| Sample no. | Incremental Stretching, First/second | Description | Basis weight (gsm) | CD peak elongation (%) | Bond length (mm) | DOE (mm) | Strain at 10 g/cm load (%) | Open area (%) | Hole size (mm²) | Hole aspect ratio | Basis weight (gsm) | Web integrity |
| 1a | First | 50/50 PE/PP bico SB, Lurgi Process (BBA) | 26 × 2 | 142 | 2.54 | 2.03 | 56 | 23.3 | 3.3 | 2.4 | 18 | Good |
| 1b | Second | 50/50 PE/PP bico SB, Lurgi Process (BBA) | " | " | — | >1.52 | | Web has no integrity | | | | Poor (shreds) |
| 2a | First | 50/50 PE/PP bico SB, Slot-draw Process (BBA) | 50 | 353 | 2.54 | 2.54 | 35 | 16.5 | 2.2 | 2.6 | 27.2 | Good |
| 2b | Second | 50/50 PE/PP bico SB, Slot-draw Process (BBA) | " | " | — | 2.41 | 141 | 16.9 | 2.1 | 2.6 | 30.9 | Good |
| 3a | First | 50/50 PE/coPP bico SB, Slot-draw Process (BBA) | 45 | 212 | 3.81 | 2.41 | 59 | 22.0 | 4.1 | 4.2 | 29.9 | Good |
| 3b | Second | 50/50 PE/coPP bico SB, Slot-draw Process (BBA) | " | " | — | 2.29 | 115 | 23.6 | 3.8 | 3.1 | 30 | Good |
| 4a | First | 80/20 + 50/50 PE/PP bico SB, Slot-draw process (BBA) | 29 × 2 | 80/20: 148; 50/50: 325 | 3.81 | 1.78 | 64 | 19.5 | 2.8 | 3.7 | 41.2 | Good |
| 4b | Second | 80/20 + 50/50 PE/PP bico SB, Slot-draw process (BBA) | " | 80/20: 148; 50/50: 325 | — | 1.78 | 142 | — | — | — | — | Good |
| 5a | First | Softspan 200, SB nonwoven made with a PP copolymer (BBA) | 2 × 25 | 190 | 3.81 | 2.54 | 31 | 23.3 | 4.6 | 3.5 | 28.6 | Good |
| 5b | Second | Softspan 200, SB nonwoven made with a PP copolymer (BBA) | " | " | — | 2.03 | 111 | 23.6 | 4.7 | 3.5 | 30.8 | Borderline OK |
| 6a | First | 50/50 PE/PP bico SB, Lurgi Process (BBA) | 26 × 2 | 157 | 3.81 | 2.41 | 57 | 21.0 | 3.6 | 2.4 | 35.0 | Good |
| 6b | Second | 50/50 PE/PP bico SB, Lurgi Process (BBA) | " | " | — | 2.79 | 102 | 23.0 | 4.2 | 3.2 | 35.2 | OK |

As shown in Table 1 above, highly extensible apertured nonwoven webs can be produced by the method disclosed herein. CD peak elongation of the precursor web is an important processing limitation, with bond length of the melt stabilized regions being an important parameter as well.

While particular embodiments of the present invention have been illustrated and described, it would be obvious to those skilled in the art that various other combinations and modifications can be made without departing from the scope of the invention. It is therefore intended to cover in the appended claims all such combinations and modifications that are within the scope of this invention.

The invention claimed is:

1. A method for making a highly extensible apertured nonwoven web comprising the steps of:
   a) providing a nonwoven web comprising spunbond bicomponent fibers, said nonwoven web having a length measured in a machine direction and a first width measured in a cross machine direction, said nonwoven web having a peak CD extensibility of at least 150%;
   b) weakening said nonwoven web at a plurality of locations to create a plurality of weakened, melt-stabilized locations;
   c) applying a first tensioning force to said nonwoven web to cause said nonwoven web to rupture at said plurality of weakened, melt-stabilized locations creating a plurality of apertures in said nonwoven web coincident with said plurality of weakened, melt-stabilized locations, said first tensioning force causing said nonwoven web to have a second width;
   d) incrementally stretching said nonwoven to locally extend portions of said nonwoven web in a direction substantially parallel to said cross machine direction to a third width that is greater than the second width; and
   e) applying tension to said nonwoven web in the machine direction such that said nonwoven web has a width less than said third width.

2. The method of claim 1 wherein said nonwoven web includes meltblown microfibers.

3. The method of claim 1 wherein said nonwoven web is a nonelastic nonwoven web.

4. The method of claim 1 wherein said second tensioning step causes said nonwoven web to exhibit extension in the cross machine direction of at least 70% at 10 g/cm loading.

5. The method of claim 1 wherein the tension applied to said nonwoven web in the machine direction is such that said nonwoven web has a width substantially equal to said second width.

* * * * *